United States Patent
Gordon et al.

(10) Patent No.: US 9,272,101 B2
(45) Date of Patent: Mar. 1, 2016

(54) IDENTIFYING DRY NEBULIZER ELEMENTS

(75) Inventors: Benjamin Morris Gordon, Cambridge (GB); Steven David Gardner, Yaxley (GB); Thomas Edward Parker, Rampton (GB)

(73) Assignee: NEKTAR THERAPEUTICS, San Francisco, CA (US)

( * ) Notice: Subject to any disclaimer, the term of this patent is extended or adjusted under 35 U.S.C. 154(b) by 830 days.

(21) Appl. No.: 13/574,221

(22) PCT Filed: Jan. 19, 2011

(86) PCT No.: PCT/US2011/021671
§ 371 (c)(1),
(2), (4) Date: Jul. 19, 2012

(87) PCT Pub. No.: WO2011/091002
PCT Pub. Date: Jul. 28, 2011

(65) Prior Publication Data
US 2012/0291777 A1    Nov. 22, 2012

Related U.S. Application Data (60) Provisional application No. 61/296,306, filed on Jan. 19, 2010.

(51) Int. Cl.
*B05B 17/06* (2006.01)
*A61M 11/00* (2006.01)
*A61M 15/00* (2006.01)
(Continued)

(52) U.S. Cl.
CPC ......... *A61M 11/005* (2013.01); *A61M 15/0081* (2014.02); *A61M 15/0085* (2013.01); *B05B 17/0646* (2013.01); *A61M 2205/276* (2013.01);
(Continued)

(58) Field of Classification Search
CPC ............ A61M 11/005; A61M 15/0085; B05B 17/0646; B05B 17/0669; B05B 12/081
See application file for complete search history.

(56) References Cited

U.S. PATENT DOCUMENTS 4,113,809 A * 9/1978 Abair et al. ..................... 261/81
5,164,740 A    11/1992 Ivri
(Continued)

FOREIGN PATENT DOCUMENTS

CN    101461978 A    6/2009
EP    1558315    8/2005
(Continued)

OTHER PUBLICATIONS

Mexican Office Action mailed on Oct. 17, 2014 for Mexican Patent Application No. MX/a/2012/008347 filed on Jan. 19, 2011, all pages.
(Continued)

*Primary Examiner* — Justine Yu
*Assistant Examiner* — Kathrynn Lyddane
(74) *Attorney, Agent, or Firm* — Kilpatrick Townsend & Stockton LLP (57) ABSTRACT

Various arrangements for determining whether a liquid is in contact with a nebulizer element are disclosed. A nebulizer element may be energized with an electrical signal at a measurement frequency. An impedance of the nebulizer element may be measured, thereby obtaining a measured impedance value. The impedance value may be compared to a stored impedance value. Based on the comparison, it may be determined whether the liquid contacts the nebulizer element.

13 Claims, 5 Drawing Sheets

(51) Int. Cl.
*B05B 17/00* (2006.01)
*B05B 12/08* (2006.01)

(52) U.S. Cl.
CPC ........... *A61M 2205/70* (2013.01); *B05B 12/081* (2013.01); *B05B 17/0669* (2013.01)

(56) References Cited

U.S. PATENT DOCUMENTS

| | | | |
|---|---|---|---|
| 5,586,550 | A | 12/1996 | Ivri et al. |
| 5,758,637 | A | 6/1998 | Ivri et al. |
| 5,922,675 | A | 7/1999 | Baker et al. |
| 5,938,117 | A | 8/1999 | Ivri |
| 6,014,970 | A | 1/2000 | Ivri et al. |
| 6,085,740 | A | 7/2000 | Ivri et al. |
| 6,235,177 | B1 | 5/2001 | Borland et al. |
| 6,540,154 | B1 | 4/2003 | Ivri et al. |
| 6,615,824 | B2 | 9/2003 | Power |
| 6,978,779 | B2 * | 12/2005 | Haveri .................. 128/200.16 |
| 7,322,349 | B2 | 1/2008 | Power |
| 7,458,372 | B2 | 12/2008 | Feiner et al. |
| 2002/0129813 | A1 | 9/2002 | Litherland et al. |
| 2004/0031488 | A1 * | 2/2004 | Terada et al. ............ 128/203.15 |

FOREIGN PATENT DOCUMENTS

| | | |
|---|---|---|
| IN | 6298/DELNP/2012 | 9/2015 |
| JP | S53122911 A | 10/1978 |
| MX | 329332 | 4/2015 |

OTHER PUBLICATIONS

Eurasian Office Action dated Aug. 13, 2014 for Eurasian Patent Application No. 201201015 filed on Jan. 19, 2011, 2 pages.
Eurasian Office Action dated May 29, 2015 for Eurasian Patent Application No. 201201015 filed on Jan. 19, 2011, 3 pages.
Eurasian Office Action dated Aug. 13, 2014 for Eurasian Patent Application No. 201201015 filed on Jan. 19, 2011, 3 pages.
Eurasian Office Action dated Jan. 20, 2014 for Eurasian Patent Application No. 201201015 filed on Jan. 19, 2011, 3 pages.
Japanese Office Action dated Sep. 16, 2014 for Japanese Patent Application No. 2012-550081 filed Jan. 19, 2011, 3 pages.
Japanese Office Action dated Jul. 1, 2015 for Japanese Patent Application No. 2012-550081 filed Jan. 19, 2011, 3 pages.
Chinese Office Action dated Dec. 3, 2014 for Chinese Patent Application No. 201180010284.7 filed Jan. 19, 2011, all pages.
International Search Report and Written Opinion mailed Mar. 14, 2011 for International Patent Application No. PCT/US2011/021671 filed Jan. 19, 2011, 9 pages.
International Preliminary Report on Patentability mailed Mar. 14, 2011 for International Patent Application No. PCT/US2011/021671 filed Jan. 19, 2011, 11 pages.
Chinese Office Action dated Jan. 24, 2014 for Chinese Patent Application No. 201180010284.7 filed Jan. 19, 2011, all pages.
Chinese Office Action dated Aug. 7, 2014 for Chinese Patent Application No. 201180010284.7 filed Jan. 19, 2011, all pages.
Israeli Office Action dated Nov. 12, 2014 for Israeli Patent Application No. 220886, filed Jul. 11, 2012, all pages.

* cited by examiner

IDENTIFYING DRY NEBULIZER ELEMENTS

CROSS-REFERENCES TO RELATED APPLICATIONS

This application is a PCT application of U.S. Patent Application No. 61/296,306 filed Jan. 19, 2010, entitled "METHODS, DEVICES AND SYSTEMS FOR IDENTIFYING DRY NEBULIZER ELEMENTS," the entire disclosure of which is incorporated herein by reference for all purposes.

This application is related to application number PCT/US2010/042473, filed Jul. 19, 2010, and U.S. Application No. 61/226,591 entitled SYSTEMS AND METHODS FOR DRIVING SEALED NEBULIZERS, filed on Jul. 17, 2009, the entire disclosures of which are incorporated by reference for all purposes. This application is also related to application PCT/US2010/042471, filed Jul. 19, 2010, and U.S. Application No. 61/226,567 entitled NEGATIVELY BIASED SEALED NEBULIZERS SYSTEMS AND METHODS, filed on Jul. 17, 2009, the entire disclosures of which are incorporated by reference for all purposes.

BACKGROUND

Embodiments described herein relate to nebulizers. In particular, the embodiments described herein relate to measuring the impedance of a nebulizer element to determine whether the nebulizer element is in contact with a liquid.

A wide variety of procedures have been proposed to deliver a drug to a patient. In some drug delivery procedures, the drug is a liquid and is dispensed in the form of fine liquid droplets for inhalation by a patient. A patient may inhale the drug for absorption through lung tissue. Such a mist may be formed by a nebulizer. Operation of a nebulizer without a liquid present may result in damage to the nebulizer.

SUMMARY

Impedance measurements may be used to determine whether a liquid is in contact with a nebulizer element. A nebulizer element may be energized with an electrical signal at a measurement frequency. An impedance of the nebulizer element may be measured, thereby obtaining a measured impedance value. The impedance value may be compared to a stored impedance value. Based on the comparison, it may be determined whether the liquid contacts the nebulizer element.

In some embodiments, a method for determining whether a liquid is in contact with a nebulizer element is present. The method includes energizing the nebulizer element with an electrical signal at a measurement frequency. The method also includes measuring an impedance of the nebulizer element, thereby obtaining a measured impedance value. The method further includes comparing the measured impedance value to a stored impedance value. Also, the method includes determining whether the liquid contacts the nebulizer element using the comparison between the measured impedance value and the stored impedance value.

In some embodiments, the measurement frequency is different from an atomization frequency at which the nebulizer is energized to atomize the liquid. In some embodiments, the method further includes energizing the nebulizer element with the electrical signal at one or more atomization frequencies concurrently with the nebulizer element being energized by the electrical signal at the measurement frequency. In some embodiments, the method further includes atomizing the liquid while the impedance of the nebulizer element is being measured. In some embodiments, the method further includes, if the nebulizer element is determined to not be in contact with liquid, disabling the nebulizer element such that the nebulizer element is not energized by the voltage at an atomization frequency. In some embodiments, the method further includes, if the nebulizer element is determined to be in contact with the liquid, energizing the nebulizer element with the electrical signal at an atomization frequency. In some embodiments, the method further includes, prior to energizing the nebulizer element with the voltage at the measurement frequency, energizing the nebulizer element with the electrical signal at the atomization frequency; and prior to energizing the nebulizer element with the electrical signal at the measurement frequency, ceasing to energize the nebulizer element with the electrical signal at the atomization frequency.

In some embodiments, a system for atomizing a liquid when the liquid is in contact with a nebulizer element is present. The system includes a nebulizer. The nebulizer may include a reservoir configured to store the liquid. The reservoir may be configured to dispense the liquid to the nebulizer element. The nebulizer may also include a nebulizer element. The nebulizer element may be configured to, when energized at an atomization frequency, atomize the liquid in contact with the nebulizer element. The system may also include a control module. The control module may be configured to output an electrical signal at an atomization frequency to energize the nebulizer element. The control module may be configured to output the electrical signal at a measurement frequency to energize the nebulizer element. The control module may also be configured to measure an impedance of the nebulizer element, thereby obtaining a measured impedance value. The control module may further be configured to compare the measured impedance value to a stored impedance value. Also, the control module may be configured to determine whether the liquid contacts the nebulizer element using the comparison between the measured impedance value and the stored impedance value.

In some embodiments, a computer program product residing on a non-transitory processor-readable medium and comprising processor-readable instructions is presented. The instructions, when executed, may cause the processor to: cause a nebulizer element to energize with an electrical signal at a measurement frequency; cause an impedance of the nebulizer element to be measured, thereby obtaining a measured impedance value; compare the measured impedance value to a stored impedance value; and determine whether the liquid contacts the nebulizer element using the comparison between the measured impedance value and the stored impedance value.

BRIEF DESCRIPTION OF THE DRAWINGS

A further understanding of the nature and advantages of the present invention may be realized by reference to the following drawings.

FIG. 1 illustrates an embodiment of a nebulizer.

FIG. 2 illustrates an embodiment of a nebulizer driven by a control module.

FIG. 3 illustrates a graph of the impedance of a wet nebulizer element and a dry nebulizer element at various frequencies.

FIG. 4 illustrates an embodiment of a method for determining if liquid is in contact with a nebulizer element.

FIG. 5 illustrates another embodiment of a method for determining if liquid is in contact with a nebulizer element.

DETAILED DESCRIPTION

Operation of a nebulizer without a liquid present may result in damage to the nebulizer and/or the nebulizer's element. As such, it may be desirable to avoid energizing a nebulizer's element when the element is dry. Various implementations are described for determining whether a nebulizer element is in contact with a liquid (the nebulizer element is wet) or is not in contact with a liquid (the nebulizer element is dry).

More specifically, the invention involves measuring the impedance of a nebulizer element and comparing the measurement to a predetermined impedance value. This comparison is used to determine whether the nebulizer element is in contact with a liquid or not. By measuring the impedance of a nebulizer element at one or more frequencies, it may be determined whether a liquid is in contact with the nebulizer element.

There are various situations where a nebulizer element may potentially be operated dry. For example, a liquid (for example, a liquid drug, such as Amikacin) may have previously been in contact with a nebulizer element, but the supply of liquid may have become exhausted. A particular dose of such a liquid drug may be provided to a nebulizer element to be atomized for delivery to a patient. At the end of the dose, the nebulizer element may continue to be energized although the entire dose of the liquid drug has been atomized, thus resulting in a dry nebulizer element being energized. As another example, a nebulizer element may inadvertently be energized without any liquid being in contact with to the nebulizer element. In both of these instances, the nebulizer and/or its element may be damaged by being energized while dry.

Figure 1:
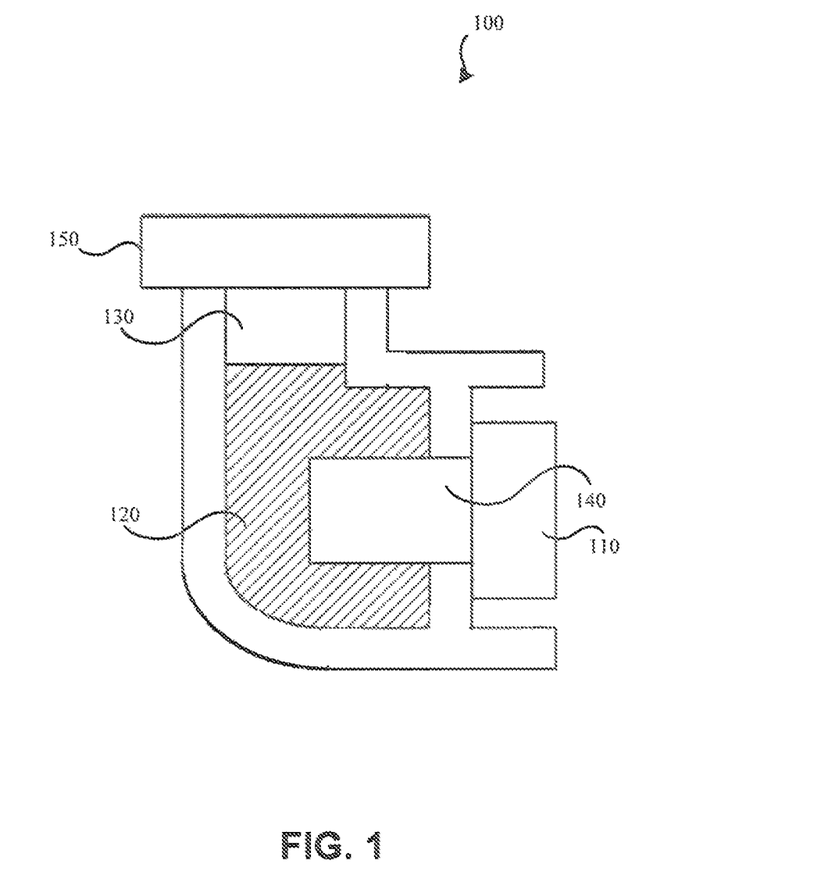
Figure 2:
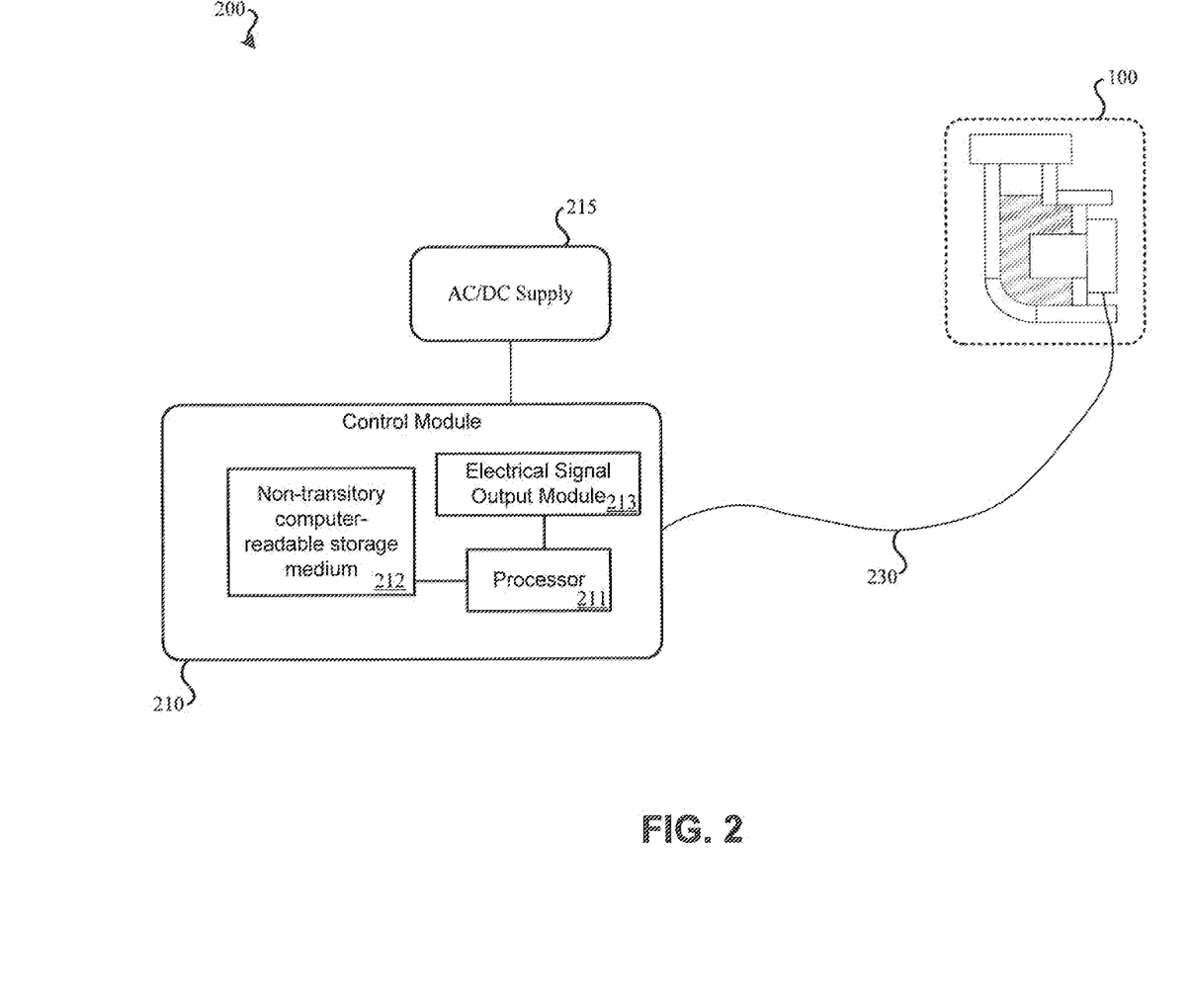
Figure 3:
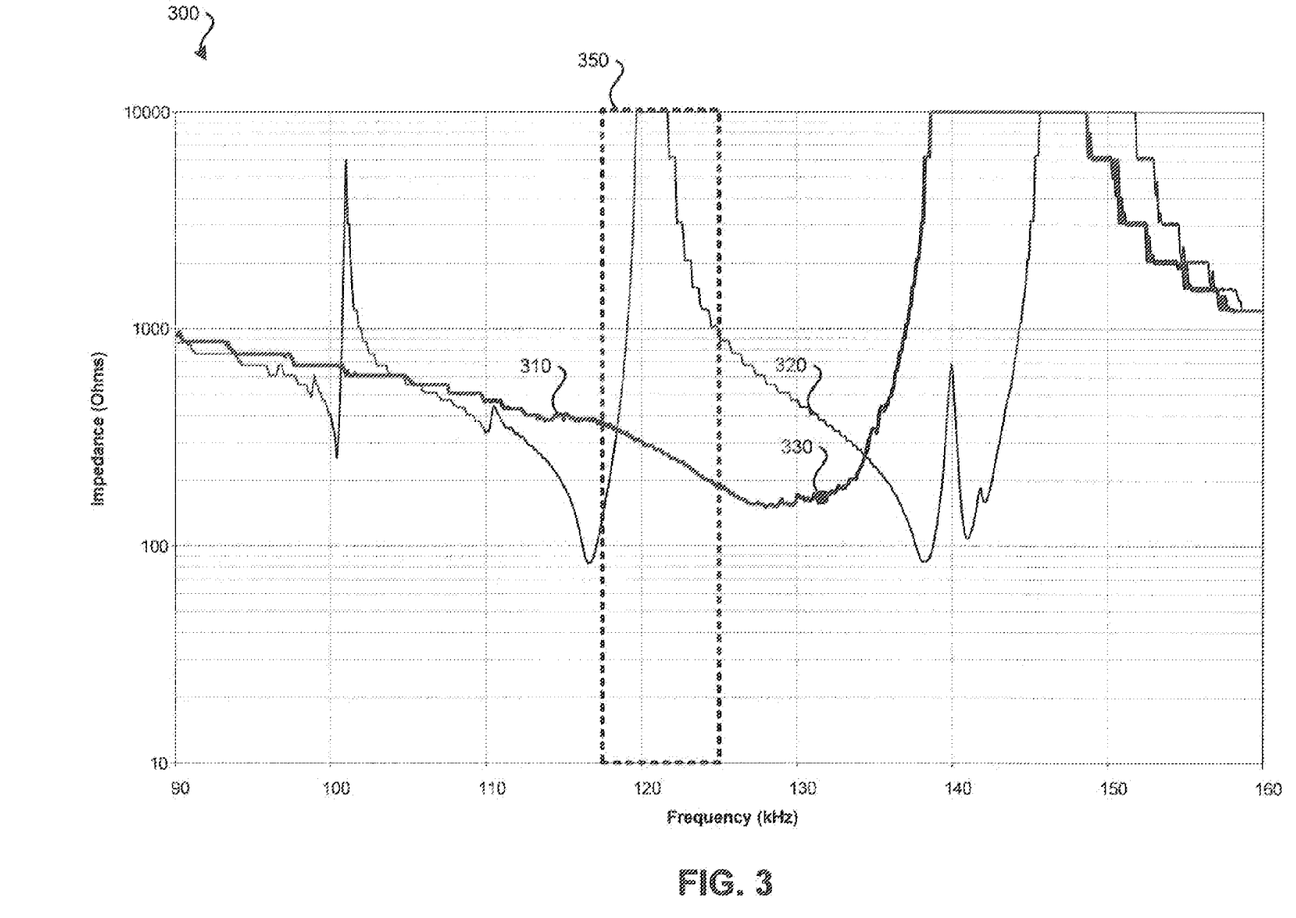
Figure 4:
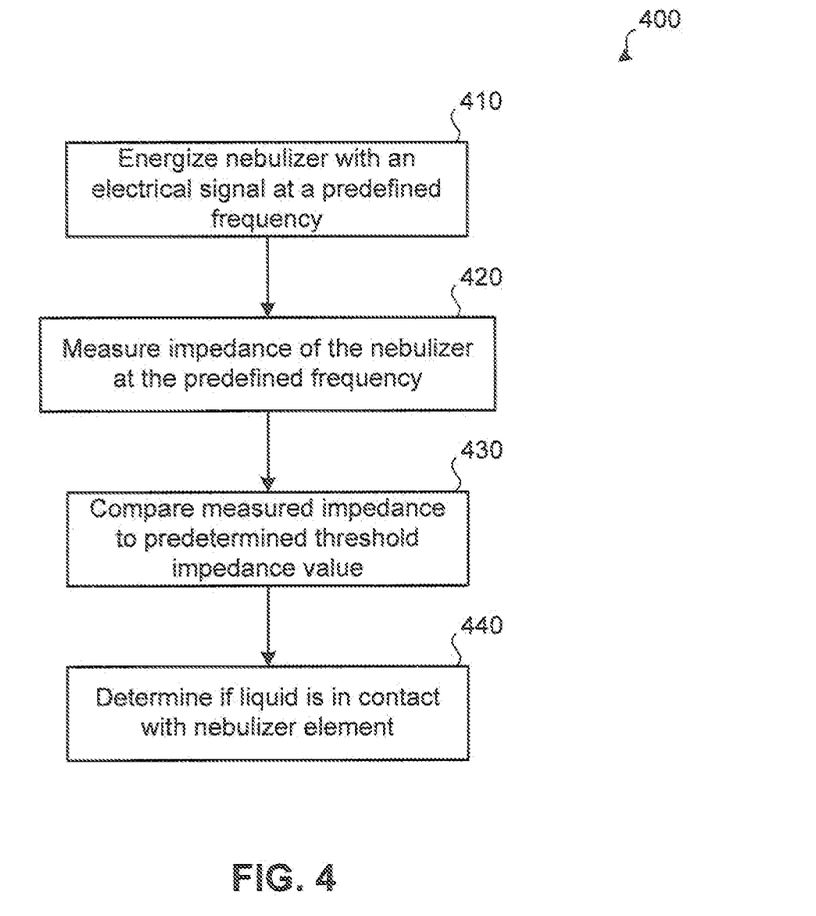

FIG. 1 illustrates an embodiment of a nebulizer 100. The nebulizer 100 may include nebulizer element 110, drug reservoir 120, head space 130, interface 140, and cap 150. Nebulizer element 110 may be comprised of a piezoelectric ring that expands and contracts when an electric signal is applied. The piezoelectric ring may be attached to a perforated membrane. Such a perforated membrane may have a number of holes passing through it. When an electric signal is applied to the piezoelectric ring, this may cause the membrane to move and/or flex. Such movement of the membrane while in contact with a liquid may cause the atomization of the liquid, generating a mist of liquid particles. Nebulizer element 110 may also be a vibrating aperture plate.

A supply of a liquid, commonly a liquid drug (examples of which are detailed later in this document), may be held in the drug reservoir 120. As illustrated in FIG. 1, drug reservoir 120 is only partially filled with liquid drug. As liquid drug is atomized, the amount of the liquid drug remaining in drug reservoir 120 may decrease. Depending on the amount of the liquid drug in the drug reservoir 120, only a portion of the reservoir may be filled with liquid drug. The remaining portion of drug reservoir 120 may be filled with gas, such as air. This space is referred to as head space 130. An interface 140 may serve to transfer liquid drug between drug reservoir 120 and nebulizer element 110.

Nebulizers, and the techniques associated with nebulizers, are described generally in U.S. Pat. Nos. 5,164,740; 5,938,117; 5,586,550; 5,758,637; 6,014,970; 6,085,740; 6,235,177; 6,615,824; 7,322,349, the complete disclosures of which are incorporated by reference for all purposes.

A nebulizer, such as nebulizer 100, may be connected with a control module such as illustrated in FIG. 2. FIG. 2 illustrates a simplified block diagram of an embodiment 200 of a nebulizer control module coupled with nebulizer 100. Nebulizer 100 of FIG. 2, which may represent nebulizer 100 of FIG. 1 or some other nebulizer such as those described in the referenced applications, may be connected with control module 210 via wire 230, which may be a cable. Wire 230 may allow control module 210 to transmit an electrical signal of varying frequency and varying voltage through wire 230 to nebulizer 100. Control module 210 may be connected to voltage supply 215 capable of supplying a DC voltage and/or an AC voltage to control module 210.

Control module 210 may contain various components. In some embodiments of control module 210, processor 211, non-transitory computer-readable storage medium 212, and electrical signal output module 213 are present. Processor 211 may be a general purpose processor or a processor designed specifically for functioning in control module 210. Processor 211 may serve to execute instructions stored as software or firmware. Such instructions may be stored on non-transitory computer-readable storage medium 212. Non-transitory computer-readable storage medium 212 may be random access memory, flash memory, a hard drive, or some other storage medium capable of storing instructions. Instructions stored by non-transitory computer-readable storage medium 212 may be executed by processor 211, the execution of the instructions resulting in electrical signal output module 213 generating an electrical signal of a varying frequency and/or varying voltage that is output to the nebulizer element of nebulizer 100 via wire 230. The signal output by electrical signal output module 213 may include one or more frequencies. For example, electrical signal output module 213 may intermittently or concurrently generate an electrical signal that at one or more frequencies is used to energize the nebulizer element to measure the impedance of the nebulizer element and one or more frequencies used to energize the nebulizer element to atomize liquid.

FIG. 3 illustrates an embodiment of a graph 300 of how the impedance of a nebulizer element, such as nebulizer element 110 of FIG. 1, may vary depending on the frequency of an applied electrical signal and whether the nebulizer element is wet or dry. Line 310 represents the impedance of the nebulizer element when wet at various frequencies. Line 320 represents the impedance of the nebulizer element when dry at various frequencies. Depending on the frequency of the applied electrical signal, a wet nebulizer element may have a higher, lower, or the same impedance as a dry nebulizer element. In order to determine whether a nebulizer element is in contact with a liquid (e.g., whether it is wet or dry), the frequencies where the impedances greatly diverge between wet and dry states may be analyzed. For example, a frequency of roughly 122 kHz may be used. At roughly 122 kHz, in region 350, which has been denoted by a dotted box as a frequency range where the impedances of the nebulizer vary greatly between wet and dry states, the wet nebulizer has an impedance of approximately 280 ohms. At the same frequency, the same nebulizer element not in contact with a liquid has an impedance of over 10,000 ohms. As those with skill in the art will recognize, differing results may be achieved for different nebulizers and/or nebulizer elements. As such, for different nebulizers and/or nebulizer elements, different frequencies may be preferable for determining whether the nebulizer element is wet or dry. Point 330 may represent the frequency (and associated impedance) at which this nebulizer element is typically energized to atomize liquid. As such, the frequency used to determine whether the nebulizer element is wet or dry may be a frequency different from the frequency used to atomize liquid. Such a graph may be produced for each design of nebulizer and/or nebulizer element to identify one or more frequencies to be used to determine whether an element is wet or dry and to determine the impedance values associated with the wet and dry states.

The impedance of the nebulizer element used to produce the graph of FIG. 3 may be measured around a frequency of 120 kHz to determine whether the nebulizer element is wet or dry. The impedance may be monitored through a method such as method 400 of FIG. 4. FIG. 4 illustrates an embodiment of a method for determining whether a nebulizer element is wet or dry. Method 400 may be performed using a nebulizer such as nebulizer 100 of FIG. 1, and a control module, such as control module 210 of FIG. 2. At block 410, the nebulizer element may be energized by an electrical signal at a frequency generated by a control module. The characteristics of the nebulizer element being energized may have already been analyzed at various voltages and frequencies, such as the nebulizer element used to produce the graph of FIG. 3. Therefore, it may already be known at what frequency or frequencies and/or voltages the impedance of the nebulizer element while wet varies significantly from the impedance of the nebulizer element while dry. For example, if the nebulizer element being used while performing method 400 is the nebulizer element used to create FIG. 3, the nebulizer element may be energized at a measurement frequency around 120 kHz. This frequency may have been selected due to the large difference in the impedance of the nebulizer element when wet compared to dry.

Once the nebulizer element is energized with an electrical signal at a measurement frequency at block 410, the impedance of the nebulizer element may be measured at block 420. The measurement frequency may be the same or a frequency different from the frequency used to energize the nebulizer element to atomize liquid. If the frequencies are different, the control module may temporarily suspend exciting the nebulizer element with the atomization frequency. In some embodiments, the nebulizer element may be excited with the atomization frequency and the measurement frequency at the same time. It some embodiments, more than one atomization frequency and/or more than one measurement frequency may be excited at the same time. The impedance may be measured by a control module, such as control module 210 of FIG. 2. This measured impedance value may be stored by the control module using non-transitory computer-readable storage medium 212 or some other storage device.

This measured impedance value may then be compared to a predetermined impedance value at block 430. This predetermined impedance value may have been determined empirically during a previous analysis of the characteristics of the nebulizer element while wet and dry. For example, again assuming method 400 is using the nebulizer element used to produce the graph of FIG. 3, the predetermined impedance value may be a threshold value, such as 1100 ohms for a frequency of 122 kHz. Therefore, if the measured impedance is determined to be greater than 1100 ohms at this frequency, the nebulizer element is likely dry; if the measured impedance is determined to be less than 1100 ohms at this frequency, the nebulizer element is likely wet.

At block 440, based upon the comparison at block 430, it may be determined if a liquid is or is not in contact with the nebulizer element. Based upon such a determination, different courses of action may be taken. For example, if it is determined that the nebulizer element is dry, the nebulizer element may cease to be energized, thereby preventing possible damage to the nebulizer element. If it is determined that the nebulizer element is wet, the nebulizer element may continue to be energized by the electrical signal at a frequency used to atomize liquid, thereby continuing to cause the nebulizer element to atomize the liquid, such as to produce a dose of medicine for inhalation by a patient.

Such a process may be used to determine whether a nebulizer element is wet or dry at any point during nebulizer operation. For example, initially upon being energized, a method, such as method 400, may be used to determine whether any liquid is in contact with the nebulizer element. As such, the process may be used to prevent the nebulizer element from initially being energized if a person neglected to add liquid the reservoir of the nebulizer. In some embodiments, periodically or intermittently during operation, method 400 may be performed to determine if the nebulizer's supply of liquid has been exhausted.

Figure 5:
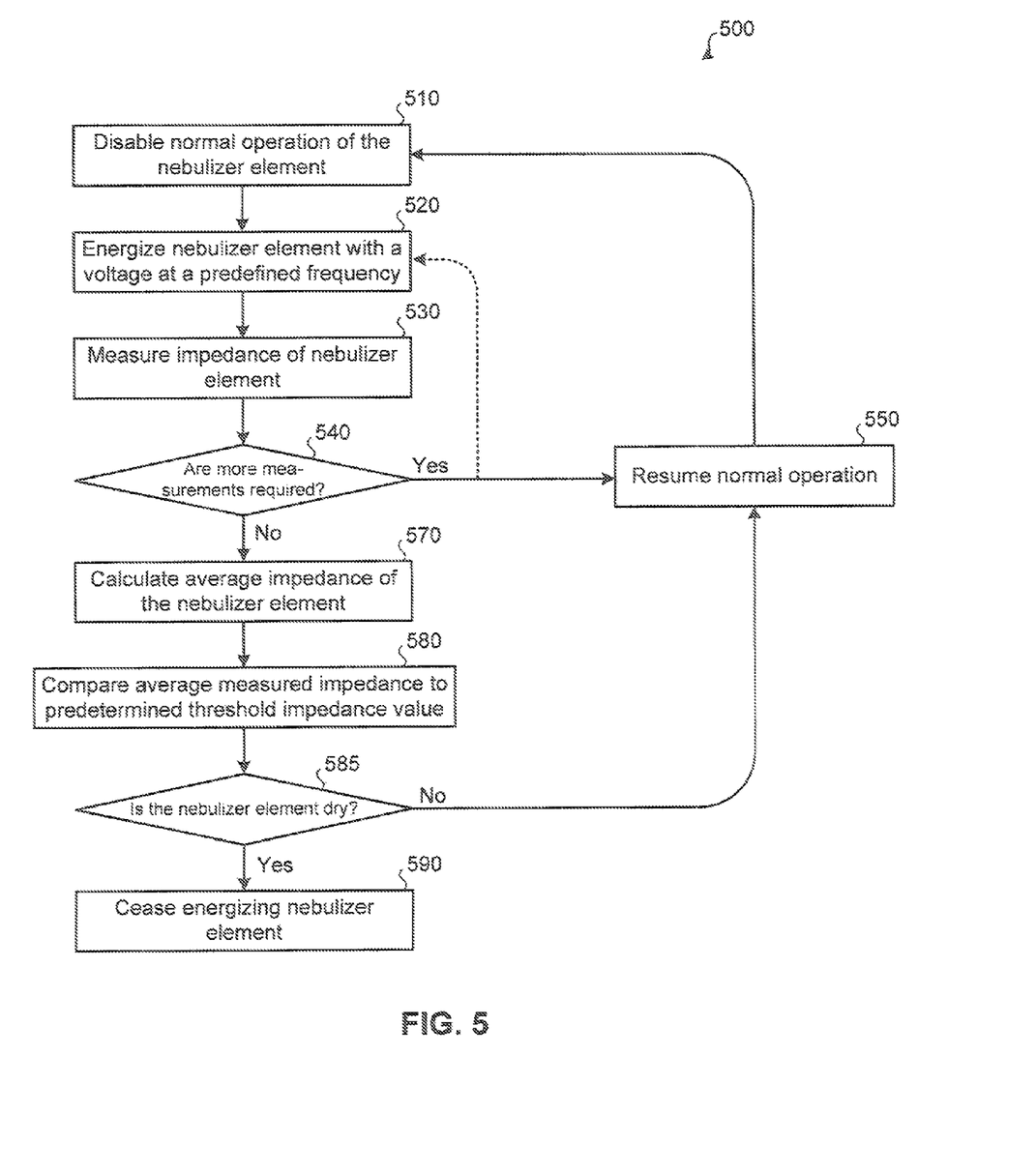

Besides measuring impedance at one frequency, a more accurate determination of whether a nebulizer element is wet or dry may be performed by measuring a number of different impedance values at one or multiple frequencies for comparison to one or more predetermined impedance values. FIG. 5 illustrates a method 500 where the impedance of a nebulizer element is measured at multiple frequencies. An average impedance is calculated from the measurements at these various frequencies and may be compared to a predetermined impedance value to determine if the nebulizer element is likely wet or dry.

At block 510, normal operation of a nebulizer, such as nebulizer 100 of FIGS. 1 and 2, may be disabled, such as by control module 210 of FIG. 2. Disabling may include the nebulizer element ceasing to be energized by an electrical signal at one or more frequencies being used to atomize liquid. This may be necessary if prior to block 510 the nebulizer element was atomizing a liquid. If the nebulizer has not begun atomizing a liquid, such as immediately upon power up, block 510 may not be necessary. In some embodiments, the nebulizer element may be excited by a frequency used to measure impedance (e.g., a measurement frequency) and by a frequency used to atomize liquid (e.g., an atomization frequency) at the same time; as such, disabling atomization may not be necessary. At block 520, the nebulizer element may be energized by an electrical signal at a predetermined voltage and/or one or more predetermined frequencies. For example, assuming the nebulizer element used in method 500 is the same nebulizer element as used to produce graph 300 of FIG. 3, the voltage used may be 5 V and the first frequency used may be 118 kHz.

At block 530, the impedance of the nebulizer element may be measured. This impedance value may be measured and stored by a control module, such as control module 210 of FIG. 2, using non-transitory computer-readable storage medium 212.

At block 540, it may be determined whether other impedance measurements are to be collected prior to comparing the one or more measured impedance values to one or more predetermined impedance values. If the answer is yes, returning to block 520 (via the illustrated dotted path), the nebulizer element may immediately be energized using an electrical signal at a frequency necessary to conduct the next impedance measurement. In some embodiments, the nebulizer element is energized at the same frequency used at block 520 to repeat the same measurement. In some embodiments, a different frequency is used.

Alternatively, in some embodiments, the nebulizer may resume normal operation at block 550 and atomize liquid at an atomization frequency. After some period of time performing normal operation (e.g., a tenth of a second, several seconds, a minute), normal operation may again be disabled (e.g., ceasing to energize the nebulizer element with the electrical signal at the atomization frequency) at block 510, with the nebulizer element being energized at the voltage and frequency necessary for the next impedance measurement at block 520. Here, the frequency may be the same measurement frequency or a different measurement frequency as previously used at block 520.

The time period of normal operation may be determined by how often it is desired that a determination of whether the nebulizer element is wet or dry be made. For example, if a total of six frequency measurements is to be collected before comparison to a predetermined impedance value, and it is wished that the nebulizer unit determine whether the nebulizer element is wet or dry every 10 seconds, this would mean that the impedance of the nebulizer element at a frequency would need to be collected at least every 1.6 seconds if a period of normal operation is to occur between impedance measurements. This loop of either 1) immediately energizing at the different voltage and/or frequency or 2) resuming normal operation and energizing at a different voltage and/or frequency may continue until a predetermined number and impedance measurements at different voltages and/or frequencies have been collected. For example, referring again to the nebulizer element used to produce the graph of FIG. 3, besides 118 kHz, impedance measurements may also be collected at 119.5 kHz, 121 kHz, 122.5 kHz, 124 kHz, and 125.5 kHz.

Once it is determined at block 540 that no additional measurements of impedance values at different voltages and/or frequencies are to be collected, the process may continue to block 570. At block 570, collected impedance values at the various frequencies may be used to calculate an average measured impedance. At block 580, this average measured impedance may be compared to a predetermined, stored average impedance value. The comparison may involve determining whether the average measured impedance value is greater than, equal to, or less than the predetermined impedance value.

In some embodiments, rather than comparing an averaged measured impedance value to a stored average impedance value, the individual measured impedance values may be compared to individual stored impedance threshold values for each frequency. If the majority of comparisons indicate a wet nebulizer element, the nebulizer element may be identified as wet. If the majority of comparisons indicate a dry nebulizer element, the nebulizer element may be identified as dry.

If, at block 585, the nebulizer element is determined to be dry, the nebulizer element may be disabled at block 590. Disabling may include ceasing energizing the nebulizer element at one or more frequencies. If the nebulizer was previously atomizing a liquid drug during normal operation, the nebulizer element being determined to be dry may indicate that the entire dose of the drug has been delivered.

If, at block 585, the nebulizer element is not dry (e.g., it is wet), at block 550 the nebulizer may resume normal operation with the nebulizer element being energized at one or more atomization frequencies. Normal operation may continue for a predetermined amount of time, after which method 500, with new impedance measurements being conducted at each of the frequencies, may be repeated. Method 500 may continuously repeat until the nebulizer is determined to be dry at block 585 or some intervening event ceases operation of the nebulizer. In some embodiments, another process may result in the nebulizer being disabled, such as expiration of a predetermined amount of time or receiving user input.

As it will be understood by those with skill in the art, impedance relates to a ratio of voltage and current. If either the current or voltage is known, than the impedance can be determined using either a measured voltage or measured current, respectively. For example, in the preceding described nebulizer elements, if an applied voltage is constant or inferred to be a known value, than the current measurements could be used to determine if the nebulizer element is wet or dry. Similarly, in the preceding described nebulizer elements, if an applied current is constant or inferred to be a known value, than voltage measurements could be used to determine if the nebulizer element is wet or dry. Further, if the applied voltage and current have a known relationship, then just current or voltage measurements could be used to determine if the nebulizer element is wet or dry. Moreover, in some embodiments, the amount of power absorbed by the nebulizer element could be used to determine if the nebulizer element is wet or dry. Methods 400 and 500 of FIGS. 4 and 5, respectively, may be adapted such that a constant current or constant voltage is applied to the nebulizer element, and a resulting current, voltage, or power is measured. Information such as that presented in graph 300 could be gathered for various applied constant voltages or constant currents to determine at what magnitudes dry nebulizer elements and wet nebulizer elements diverge in measured current, voltage, or power. As such, embodiments of the invention exist that rely on voltage, current, and/or power measurements, rather than just impedance. Further, in some embodiments, measurements of multiple different values (such as a voltage measurement when a constant current is applied and a current measurement when a constant voltage is applied) may be taken. Using multiple measurements may improve the accuracy of determining whether the nebulizer element is wet or dry. For example, to determine the nebulizer element is dry and cease energizing the nebulizer element, both measurements may need to be in agreement that a dry nebulizer is present, otherwise the nebulizer element may continue to be energized.

While a wide variety of drugs, liquids, liquid drugs, and drugs dissolved in liquid may be aerosolized, the following provides extensive examples of what may be aerosolized. Additional examples are provided in U.S. application Ser. No. 12/341,780, the entire disclosure of which is incorporated herein for all purposes. Nearly any anti-gram-negative, anti-gram-positive antibiotic, or combinations thereof may be used. Additionally, antibiotics may comprise those having broad spectrum effectiveness, or mixed spectrum effectiveness. Antifungals, such as polyene materials, in particular, amphotericin B, are also suitable for use herein. Examples of anti-gram-negative antibiotics or salts thereof include, but are not limited to, aminoglycosides or salts thereof. Examples of aminoglycosides or salts thereof include gentamicin, amikacin, kanamycin, streptomycin, neomycin, netilmicin, paramecin, tobramycin, salts thereof, and combinations thereof. For instance, gentamicin sulfate is the sulfate salt, or a mixture of such salts, of the antibiotic substances produced by the growth of *Micromonospora purpurea*. Gentamicin sulfate, USP, may be obtained from Fujian Fukang Pharmaceutical Co., LTD, Fuzhou, China. Amikacin is typically supplied as a sulfate salt, and can be obtained, for example, from Bristol-Myers Squibb. Amikacin may include related substances such as kanamicin.

Examples of anti-gram-positive antibiotics or salts thereof include, but are not limited to, macrolides or salts thereof. Examples of macrolides or salts thereof include, but are not limited to, vancomycin, erythromycin, clarithromycin, azithromycin, salts thereof, and combinations thereof. For instance, vancomycin hydrochloride is a hydrochloride salt of vancomycin, an antibiotic produced by certain strains of *Amycolatopsis orientalis*, previously designated *Streptomyces orientalis*. Vancomycin hydrochloride is a mixture of related substances consisting principally of the monohydrochloride of vancomycin B. Like all glycopeptide antibiotics, vancomycin hydrochloride contains a central core heptapeptide. Vancomycin hydrochloride, USP, may be obtained from Alpharma, Copenhagen, Denmark.

In some embodiments, the composition comprises an antibiotic and one or more additional active agents. The additional active agent described herein includes an agent, drug, or compound, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system.

Examples of additional active agents include, but are not limited to, anti-inflammatory agents, bronchodilators, and combinations thereof.

Examples of bronchodilators include, but are not limited to, beta-agonists, anti-muscarinic agents, steroids, and combinations thereof. For instance, the steroid may comprise albuterol, such as albuterol sulfate.

Active agents may comprise, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, additional anti-infectives (antivirals, antifungals, vaccines) antiarthritics, antimalarials, antiemetics, anepileptics, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 1 3-cis retinoic acid, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, teicoplanin, rampolanin, mideplanin, colistin, daptomycin, gramicidin, colistimethate, polymixins such as polymixin B, capreomycin, bacitracin, penems; penicillins including penicillinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments, derivatives, and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition), which is incorporated herein by reference in its entirety.

The amount of antibiotic or other active agent in the pharmaceutical formulation will be that amount necessary to deliver a therapeutically or prophylactically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1 wt % to about 99 wt %, such as from about 2 wt % to about 95 wt %, or from about 5 wt % to 85 wt %, of the active agent, and will also depend upon the relative amounts of additives contained in the composition. The compositions of the invention are particularly useful for active agents that are delivered in doses of from 0.001 mg/day to 100 mg/day, such as in doses from 0.01 mg/day to 75 mg/day, or in doses from 0.10 mg/day to 50 mg/day. It is to be understood that more than one active agent may be incorporated into the formulations described herein and that the use of the term "agent" in no way excludes the use of two or more such agents.

Generally, the compositions are free of excessive excipients. In one or more embodiments, the aqueous composition consists essentially of the anti-gram-negative antibiotic, such as amikacin, or gentamicin or both, and/or salts thereof and water.

Further, in one or more embodiments, the aqueous composition is preservative-free. In this regard, the aqueous composition may be methylparaben-free and/or propylparaben-free. Still further, the aqueous composition may be saline-free.

In one or more embodiments, the compositions comprise an anti-infective and an excipient. The compositions may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts sufficient to perform their intended function, such as stability, surface modification, enhancing effectiveness or delivery of the composition or the like. Thus, if present, excipient may range from about 0.01 wt % to about 95 wt %, such as from about 0.5 wt % to about 80 wt %, from about 1 wt % to about 60 wt %. Preferably, such excipients will, in part, serve to further improve the features of the active agent composition, for example by providing more efficient and reproducible delivery of the active agent and/or facilitating manufacturing. One or more excipients may also be provided to serve as bulking agents when it is desired to reduce the concentration of active agent in the formulation.

For instance, the compositions may include one or more osmolality adjuster, such as sodium chloride. For instance, sodium chloride may be added to solutions of vancomycin hydrochloride to adjust the osmolality of the solution. In one or more embodiments, an aqueous composition consists essentially of the anti-gram-positive antibiotic, such as vancomycin hydrochloride, the osmolality adjuster, and water.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also comprise a buffer or a pH adjusting agent, typically a salt prepared from an organic acid or base. Representative buffers comprise organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, celluloses and derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-beta-cyclodextrin and sulfobutylether-beta-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", 19th ed., Williams & Williams, (1995), and in the "Physician's Desk Reference", 52nd ed., Medical Economics, Montvale, N.J. (1998), both of which are incorporated herein by reference in their entireties.

It should be noted that the methods, systems, and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the embodiments may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known processes, algorithms, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Further, the preceding description generally details aerosolizing liquid drugs. However, it should be understood that liquids besides liquid drugs may be aerosolized using similar devices and methods.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

What is claimed is:

1. A method for determining whether a liquid is in contact with a nebulizer element, the method comprising:
    energizing the nebulizer element with an electrical signal at an atomization frequency;
    ceasing to energize the nebulizer element with the electrical signal at the atomization frequency;
    after ceasing to energize the nebulizer element with the electrical signal at the atomization frequency, consecutively energizing the nebulizer element with the electrical signal at a plurality of measurement frequencies;
    measuring an impedance of the nebulizer element at each of the plurality of measurement frequencies, thereby obtaining a plurality of measured impedance value;
    calculating an average measured impedance value for the plurality of measured impedance values;
    comparing the average measured impedance value to a stored threshold impedance value; and
    determining whether the liquid contacts the nebulizer element using the comparison between the average measured impedance value and the stored threshold impedance value.

2. The method of claim 1, wherein each of the plurality of measurement frequencies is different from the atomization frequency at which the nebulizer is energized to atomize the liquid.

3. The method of claim 1, further comprising:
    if the nebulizer element is determined to not be in contact with liquid, ceasing to energize the nebulizer element with the electrical signal.

4. The method of claim 1, further comprising:
    if the nebulizer element is determined to be in contact with the liquid, energizing the nebulizer element with the electrical signal at an atomization frequency.

5. A system for energizing a nebulizer element when a liquid is in contact with the nebulizer element, the system comprising:
    a nebulizer, wherein the nebulizer comprises:
        a reservoir configured to store the liquid, wherein:
            the reservoir is configured to dispense the liquid to the nebulizer element; and
        the nebulizer element, wherein:
            the nebulizer element is configured to, when energized by an electrical signal at an atomization frequency, atomize the liquid in contact with the nebulizer element; and
    a control module, wherein the control module is configured to:
        output the electrical signal at the atomization frequency to energize the nebulizer element;
        cease to output the electrical signal at the atomization frequency to energize the nebulizer element;
        after ceasing to output the electrical signal at the atomization frequency, consecutively output the electrical signal at a plurality of measurement frequencies to energize the nebulizer element;
        measure an impedance of the nebulizer element at each of the plurality of measurement frequencies, thereby obtaining a plurality of measured impedance values;
        calculate an average measured impedance value for the plurality of measured impedance values;
        compare the average measured impedance value to a stored impedance value; and
        determine whether the liquid contacts the nebulizer element using the comparison between the average measured impedance value and the stored impedance value.

6. The system of claim 5, wherein each of the plurality of measurement frequencies is different from the atomization frequency.

7. The system of claim 5, wherein, if the nebulizer element is determined by the control module to not be in contact with the liquid, the control module is configured to disable the nebulizer element such that the nebulizer element is not energized by the electrical signal at the atomization frequency.

8. The system of claim 5, wherein, if the nebulizer element is determined by the control module to be in contact with liquid, the control module is configured to re-energize the nebulizer element at the atomization frequency after ceasing to energize the nebulizer element with the electrical signal at the atomization frequency.

9. A non-transitory processor-readable medium comprising processor-readable instructions configured to cause a processor to:
    cause a nebulizer element to energize with an electrical signal at an atomization frequency;
    cause the nebulizer element to cease energizing with the electrical signal at the atomization frequency;
    after ceasing to energize the nebulizer element with the electrical signal at the atomization frequency, cause the nebulizer element to energize with the electrical signal at a plurality of measurement frequencies consecutively;
    cause an impedance of the nebulizer element to be measured at each of the plurality of measurement frequencies, thereby obtaining a plurality of measured impedance values;
    calculate an average measured impedance value for the plurality of measured impedance values;
    compare the average measured impedance value to a stored threshold impedance value; and
    determine whether the liquid contacts the nebulizer element using the comparison between the average measured impedance value and the stored threshold impedance value; and control energization of the nebulizer element based on determining whether the liquid contacts the nebulizer element.

10. The non-transitory processor-readable medium of claim 9, wherein the plurality of measurement frequencies are each different from the atomization frequency at which the nebulizer element is energized to atomize the liquid.

11. The non-transitory processor-readable medium of claim 9, wherein the processor-readable instructions that cause the processor to control energization of the nebulizer element based on determining whether the liquid contacts the nebulizer element comprise processor-readable instructions that, when executed, cause the processor to:

if the nebulizer element is determined to not be in contact with liquid, cause the nebulizer element to cease being energized by the electrical signal at the atomization frequency.

12. The non-transitory processor-readable medium of claim 9, wherein the processor-readable instructions that cause the processor to control energization of the nebulizer element based on determining whether the liquid contacts the nebulizer element comprise processor-readable instructions that, when executed, cause the processor to:
if the nebulizer element is determined to be in contact with liquid, cause the nebulizer element to be energized at the atomization frequency.

13. A method for determining whether a liquid is in contact with a nebulizer element, the method comprising:
energizing the nebulizer element with an electrical signal at an atomization frequency;
ceasing to energize the nebulizer element with the electrical signal at the atomization frequency;
after ceasing to energize the nebulizer element with the electrical signal at the atomization frequency, consecutively energizing the nebulizer element with the electrical signal at a plurality of measurement frequencies;
measuring an electrical characteristic at each of the plurality of measurement frequencies of the nebulizer element, thereby obtaining a plurality of measured electrical characteristic value;
comparing the average measured electrical characteristic value to a stored threshold electrical characteristic value; and
determining whether the liquid contacts the nebulizer element using the comparison between the average measured electrical characteristic value and the stored threshold electrical characteristic value.

* * * * *